United States Patent [19]

Bruna et al.

[11] Patent Number: 5,692,492

[45] Date of Patent: Dec. 2, 1997

[54] HAND-HELD INHALATION-ACTUATED SPRAY DEVICE

[75] Inventors: Pascal Bruna, Rouen; Jacques Buffet, Villemomble, both of France

[73] Assignee: Valois S.A., Le Neubourg, France

[21] Appl. No.: 505,268

[22] PCT Filed: Feb. 15, 1994

[86] PCT No.: PCT/FR94/00166

§ 371 Date: Sep. 27, 1995

§ 102(e) Date: Sep. 27, 1995

[87] PCT Pub. No.: WO94/19040

PCT Pub. Date: Sep. 1, 1994

[30] Foreign Application Priority Data

Feb. 16, 1993 [FR] France ................... 93 01734

[51] Int. Cl.[6] ................... A61M 11/00
[52] U.S. Cl. ................... 128/200.23; 128/200.14; 128/203.12; 128/205.23
[58] Field of Search ................... 128/200.14, 205.23, 128/200.23, 200.24, 203.24, 203.12, 200.17, 203.15

[56] References Cited

U.S. PATENT DOCUMENTS

| 4,109,656 | 8/1978 | Goethel et al. | 128/266 |
|---|---|---|---|
| 4,198,626 | 4/1980 | Rauscher | 340/613 |
| 4,414,972 | 11/1983 | Young et al. | 128/200.23 |
| 4,648,393 | 3/1987 | Landis et al. | 128/200.23 |
| 5,069,204 | 12/1991 | Smith et al. | 128/203.12 |
| 5,284,133 | 2/1994 | Burns et al. | 128/200.23 |
| 5,347,998 | 9/1994 | Hodson et al. | 128/200.23 |
| 5,363,842 | 11/1994 | Mishelevich et al. | 128/200.23 |
| 5,452,711 | 9/1995 | Gault | 128/200.14 |
| 5,497,764 | 3/1996 | Ritson et al. | 128/200.14 |
| 5,507,277 | 4/1996 | Rubsamen et al. | 128/200.14 |

FOREIGN PATENT DOCUMENTS

| 0186280 | 7/1986 | European Pat. Off. |
|---|---|---|
| 0414536 | 2/1991 | European Pat. Off. |
| WO9207599 | 5/1992 | WIPO |
| WO9211054 | 7/1992 | WIPO |

*Primary Examiner*—V. Millin
*Assistant Examiner*—V. Srivastava
*Attorney, Agent, or Firm*—Sughrue,Mion,Zinn,Macpeak & Seas, PLLC

[57] ABSTRACT

A hand-held inhalation-actuated spray device including a housing; tank of substance to be sprayed; a dispenser mechanism for dispensing the substance; an inhale duct; a dispenser mechanism urging device for actuating the dispenser mechanism; a locking mechanism fixed on a plate inside the housing, which includes at least one locking latch member for locking or unlocking the action of the urging device; an unlocking mechanism for displacing the latch member towards its released position while suction exists in the inhale duct; the unlocking mechanism including an electrical actuator for actuating the latch member, an electronic control circuit for the electrical actuator, a suction sensor to deliver a suction signal to the electronic control circuit on detecting suction in the inhale duct, the electronic control circuit then causing the electrical actuator to move the latch member into its released position; the device being characterized in that it further includes a position sensor for detecting that the device is in a predetermined proper orientation, in which the position sensor is connected to the electronic control circuit and the electronic control circuit is adapted to trigger actuation of the device only if the position sensor detects the predetermined proper orientation of the device.

24 Claims, 6 Drawing Sheets

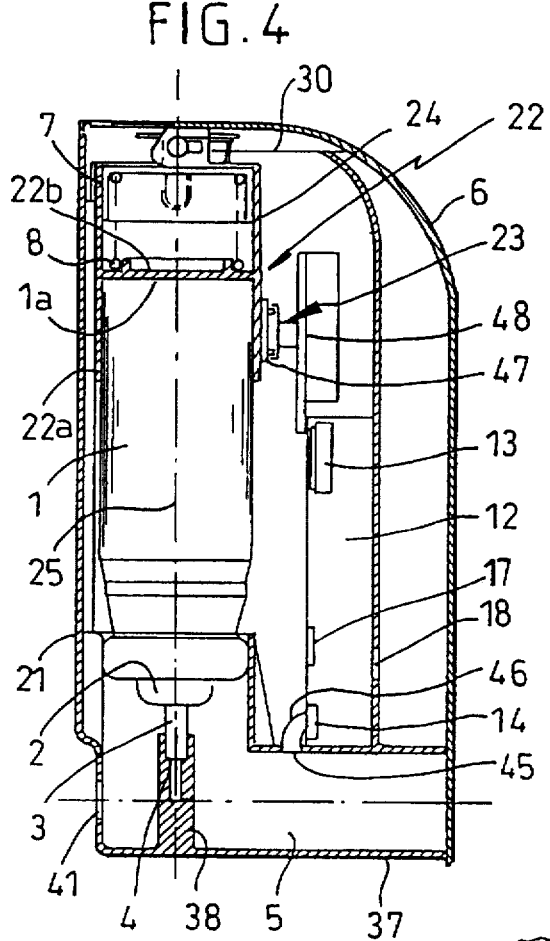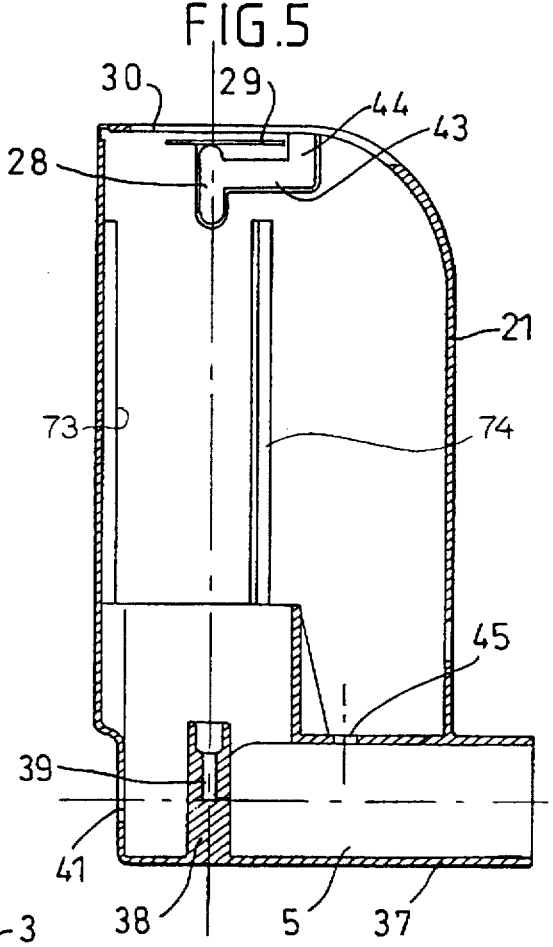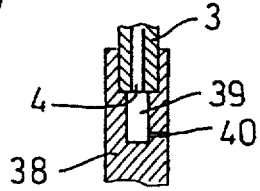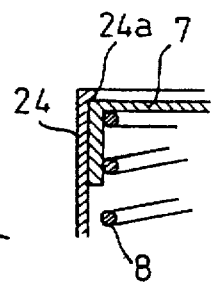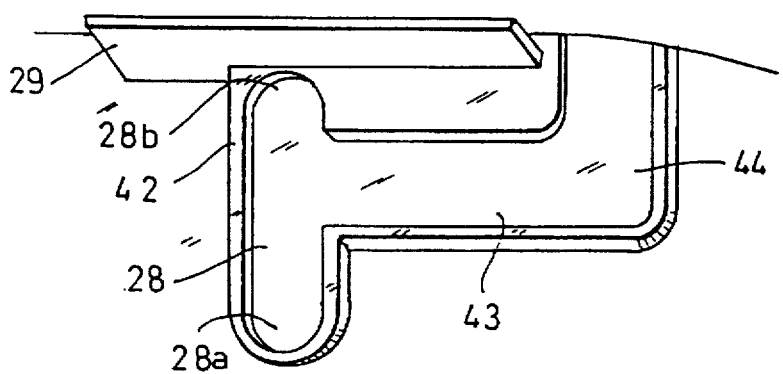

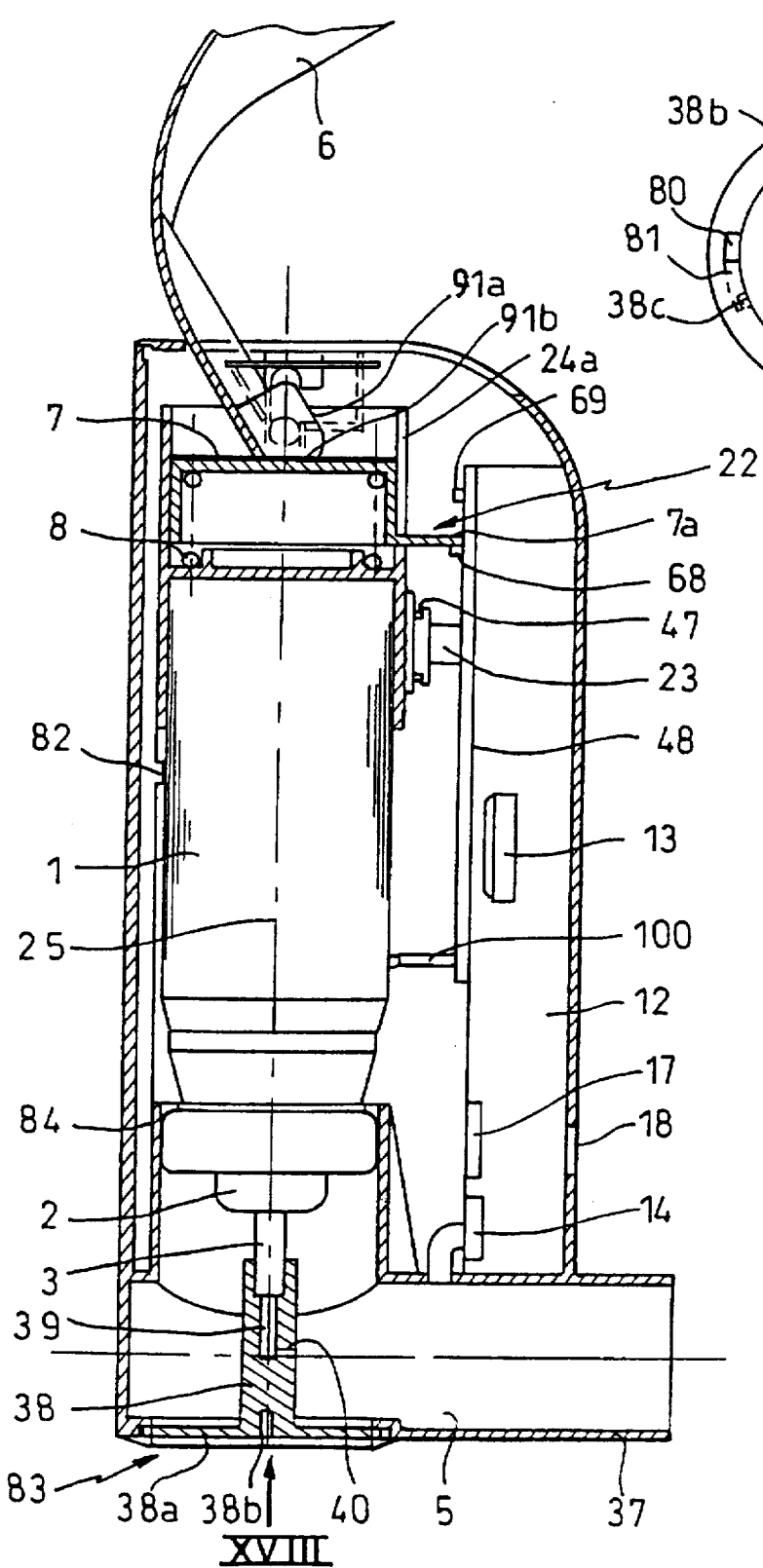
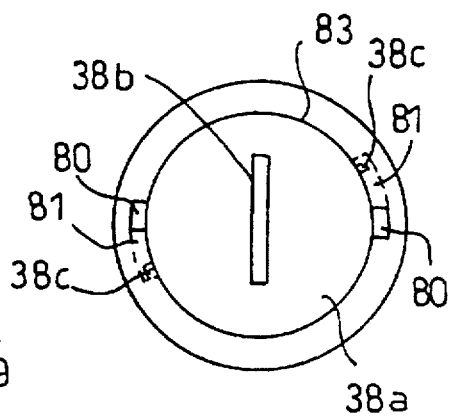

HAND-HELD INHALATION-ACTUATED SPRAY DEVICE

BACKGROUND OF THE INVENTION

The present invention relates to a hand-held inhalation-actuated spray device, and more particularly to a spray device whereby a dose of medicine is sprayed into the respiratory tract of a patient synchronously with said patient breathing in.

Numerous mechanical devices of this type are known which comprise:

- a tank of substance to be sprayed;
- a dispenser device having an actuator member that is movable between a rest position and an actuated position, said dispenser device issuing a measured amount of said substance when the actuator member is displaced from its rest position to its actuated position, said actuator member being urged resiliently towards its rest position, the dispenser device also having an outlet for issuing said substance;
- an inhale duct through which a patient can suck in air, and which communicates with said outlet for said substance;
- actuator member urging means for urging said actuator member towards its actuated position;
- a latch member movable between a latching position in which it locks said actuator member urging means, and a released position in which it no longer locks said urging means; and
- unlocking means for displacing said latch member towards its released position while suction is being applied to said inhale duct.

In purely mechanical devices, the means for unlocking the locking mechanism generally include a flap that is displaceable by the patient inhaling. The examples of such devices are given in the following documents: U.S. Pat. No. 3,456,645, U.S. Pat. No. 3,456,646, U.S. Pat. No. 3,598,294, U.S. Pat. No. 3,605,738, U.S. Pat. No. 3,636,949, U.S. Pat. No. 3,732,864, U.S. Pat. No. 3,789,843, U.S. Pat. No. 3,814,297, GB-A-1 392 192, CH-A-511 063, FR-A-2 615 106, FR-A-2 658 081, EP-A-0 147 028 (and corresponding patent U.S. Pat. No. 4,664,107), EP-A-0 414 536, EP-A-0 428 380, EP-A-0 045 419, DE-A-30 40641, DE-A-40 15367, and DE-U-89 12098.

Those purely mechanical devices suffer from the drawback that the energy required for passing the locking mechanism from its locked state to its unlocked state is provided solely by the patient breathing in, so they therefore require the patient to breath quite hard. In such systems, it is very difficult to minimize the energy that the patient must provide in order to pass the locking system from its locked state to its unlocked state since that could cause untimely operation of the device. Unfortunately, such devices need to be used even by people who are incapable of breathing in hard, such as children, old people, sufferers of asthma, people who are weak, etc. . . . .

In addition, in prior art devices, the amount of suction required to trigger spraying depends on friction between mechanical parts, and it is known that such friction is very difficult to control, and that it varies depending on the amount of wear. Such systems are therefore relatively inaccurate as to the amount of suction required to trigger spraying.

SUMMARY OF THE INVENTION

An object of the present invention is to eliminate the above drawbacks.

The present invention thus provides a device of the above-mentioned type, comprising:

- an electrical actuator for displacing said latch member;
- an electronic control circuit connected to said electrical actuator for the purpose of controlling it;
- a source of energy for powering said electronic control circuit; and
- a suction sensor for applying a suction signal to said electronic control circuit on detecting suction in the inhale duct, the electronic control circuit then causing the electrical actuator to displace the latch member into its released position;
- the device being characterized in that it further includes a position sensor for detecting proper orientation of said device, in which said position sensor is connected to said electronic control circuit, and said electronic control circuit is adapted to trigger actuation of the device only in the event of said position sensor detecting that the device is in said proper orientation.

Advantageously, said suction sensor measures suction in said inhale duct relative to atmospheric pressure, and delivers a signal representative of the suction to the electronic control circuit.

A technical problem encountered with sprays that are triggered by inhalation is that the suction created by the patient in the inhale duct varies depending on the patient. Thus, for a patient who does not breathe in hard, spraying may be triggered much too late in the breathing cycle, and may even not be triggered at all.

In an embodiment of the invention, this problem is solved in that said position sensor includes means for detecting a particular position of the device and for causing said electronic control circuit to operate in a calibration mode, in which case the device is not actuated when the patient sucks from the inhale duct, but instead said electronic control circuit then determines the maximum amount of suction set up in the inhale duct during suction, and it calculates and stores a trigger level of suction as a function of said maximum suction, the device subsequently being actuated only when suction greater than or equal to said trigger level of suction is detected in the inhale duct, and providing said electronic control circuit is not operating in its calibration mode. In this case, the device of the invention may include display means connected to the electronic control circuit to display a value for the air flow inhaled by the patient as a function of the suction measured in the inhale duct.

Another problem is guaranteeing good uniformity of the substance contained in the tank of the appliance, particularly when the substance is a mixture or a suspension. In an embodiment of the invention, this problem is resolved by a device including a shaking sensor for detecting shaking of said tank, in which said shaking sensor is connected to said electronic control circuit and said electronic control circuit is adapted to inhibit actuation of the device in the event of said tank not having been shaken during a second predetermined duration preceding inhalation by the patient.

When the dispenser device is an aerosol valve or a pump that sprays a liquid or a semi-liquid, it is necessary for the device to be properly oriented when the actuator member returns to its rest position so as to avoid the valve or the pump becoming unprimed.

In an embodiment, the substance to be sprayed is a liquid or a semi-liquid, the dispenser device is an aerosol valve or a pump, the electronic control circuit is connected to means for detecting displacement of the actuator member from its actuated position to its rest position, the electronic control circuit is connected to warning means, and said electronic control circuit is adapted to switch on the warning means, in the event that said displacement of the actuator member is detected while the device is not in its proper position, to warn the patient that the next dose of said substance that the device dispenses will be incomplete. Advantageously, the device includes means for actuating the valve or the pump manually, and said warning means tell the patient to actuate the valve or the pump manually for one occasion. The device may possibly include means for counting the number of doses of substance that are issued, and in which the issuing of said next dose is not counted. These dispositions are particularly useful for a metering valve or possibly for a pump that operates in an upsidedown position where single actuation is guaranteed to reprime the pump or the valve.

Advantageously, said position sensor includes a hollow column that extends vertically when the device is in its proper position, said hollow column having a bottom end provided with two electrical contacts and said hollow column containing a drop of mercury which wets the two electrical contacts when the device is in its proper position. Advantageously, said position sensor also serves as a shaking sensor, and said electronic control circuit is adapted to inhibit actuation of the device if said tank has not been shaken during a predetermined length of time preceding inhalation by the patient.

In an embodiment, said electrical actuator includes an electromagnet, the latch member being in mechanical connection with an armature that is sensitive to magnetic fields, said armature being disposed facing said electromagnet, said electromagnet including a permanently magnetized core for maintaining said armature in a waiting position, said electromagnet further including a coil, and said electronic control circuit being adapted to power said coil with a current whose direction and magnitude are adapted to cause said armature to move into an actuated position, said armature thus driving the latch member from its latching position into its released position.

Preferably, the armature includes at least one stud co-operating with said latch member, said armature being mounted to rotate on an axis and said latch member being mounted to rotate on an axis, said axes being secured to a plate, the stud driving the latch member in rotation from its latching position where it co-operates with a pin secured to the tank of substance to its released position.

In one embodiment, the electromagnet is a four-pole magnet and the armature is held in unstable equilibrium by opposing forces between identical poles while it is in its latching position, a signal from the electronic control circuit reducing the attraction force of the electromagnet in such a manner that the magnetic repulsion created by opposition between poles causes said armature to rotate towards its actuated position.

Advantageously, a second latching member is provided that is rotatably mounted on an axis secured to the plate, which member is substantially identical to the latch member and is disposed symmetrically relative to said latch member about the axis supporting the armature, said second latch member co-operating with a second pin secured to the tank of substance and being driven into its released position by a second stud disposed symmetrically to the first stud on the armature, said second latch member preventing the dispenser device from returning to its rest position.

Advantageously, the armature includes an arm extending outside the housing to enable said armature to be actuated manually, thereby enabling the latch member to be moved into its released position independently of any suction in the inhale duct.

In an embodiment, the dispenser device is secured to the tank of substance to be sprayed, the actuated position of the actuator member being such that said actuator member is moved towards said tank on passing from its rest position to its actuated position, the hand-held spray device including a housing secured to the inhale duct and to the actuator member, the hand-held spray device further including a cover hinged on said housing and movable between a closed position in which it closes the inhale duct, and an open position in which it opens the inhale duct, the hand-held spray device further including a compression spring adapted to urge the tank towards the actuator member to displace said actuator member into its actuated position, said compression spring having a first end which acts on the tank and a second end which acts on a thrust member, the cover including a lever-forming portion which bears against the thrust member when the cover is displaced into its open position, compressing the compression spring and said latch member locks the tank when it is in its latching position, the first end of the compression spring acts on an intermediate member fixed to said tank and said intermediate member includes a pin for receiving said latch member when it is in its latching position, said intermediate member then co-operating with the latch member to lock the tank.

In a particular case, the actuator member is displaceable relative to the dispenser member parallel to an axis, the cover is mounted to rotate about two pivots, and the pivots are mounted in respective elongate guide paths parallel to the axis, the pivots thus being axially displaceable along their guide paths against the force of the compression spring, and the cover further including two lateral projections that are outwardly directed, and that co-operate with respective inwardly-directed projecting surfaces of the housing to constrain the pivots to move along their guide paths while compressing the compression spring when the cover passes from its closed position to its open position. Advantageously, to enable the tank of substance and its dispenser device to be replaced, the two guide paths include two axial ends and each has an opening disposed at the same level on both guide paths in a position that is intermediate between the two axial ends of each of the guide paths, to enable the studs to escape from the guide paths when pressure is applied to the cover parallel to the axis, and simultaneously the cover is urged parallel to the axis towards said openings, the cover thus being removable from the housing, the housing including a loading opening of a size that enables the tank of substance together with its dispenser device to pass therethrough once the cover has been removed from the housing, the actuator member for the dispenser device being secured in removable manner to said housing, and the housing includes means for displacing the latch member into its released position independently of suction in the inhale duct. Advantageously, said lever-forming portion of the cover has a thrust surface in contact with the thrust member and said thrust surface includes two flats bearing against the thrust member respectively in the closed position and in the open position of the cover.

In an embodiment of the invention, the housing includes an opening of appropriate size to allow the tank together with its dispenser device to pass therethrough in order to be inserted into the housing or to be removed from the housing, and said housing further includes a support member which is secured to the actuator member and which is removably mounted in said opening.

In an embodiment, the dispenser device further includes a sensor for detecting the presence of the tank and/or the dispenser device, said sensor being connected to the electronic control circuit to prevent operation of the device in the event of said tank being absent.

In an embodiment, the device further includes a sensor for detecting the presence of the tank and/or of the dispenser device, said sensor being connected to the electronic control circuit, said electronic control circuit being adapted to count the number of tanks that have been installed in said device as a function of information from said sensor for detecting the presence thereof. Advantageously, said electronic control circuit is adapted to prevent the device being actuated if the number of tanks that have been installed in the device exceeds a predetermined number.

Other characteristics and advantages of the invention appear from the following detailed description of a particular embodiment of the invention that is given by way of non-limiting example and with reference to the accompanying drawings.

BRIEF DESCRIPTION OF THE DRAWINGS

In the drawings:

FIG. 4 is a vertical section view through the FIG. 1 device, when in the closed position;

FIG. 4a shows a detail of FIG. 4;

FIG. 4b shows another detail of FIG. 4;

FIG. 5 is a section view through the housing of the FIG. 4 device;

FIG. 6 is a perspective view showing a detail of the FIG. 5 housing;

FIG. 14 is a vertical section view through a variant of the device shown in FIG. 1; and FIG. 15 is a fragmentary underside view of the FIG. 14 device, as seen looking along XVIII.

DETAILED DESCRIPTION OF THE PREFERRED EMBODIMENTS

Figure 1:
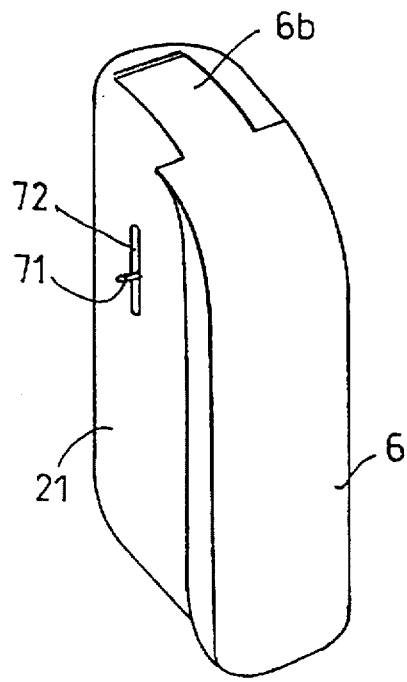
FIG. 1 is a perspective view of a device constituting an embodiment of the invention shown in its closed position.
Figure 2:
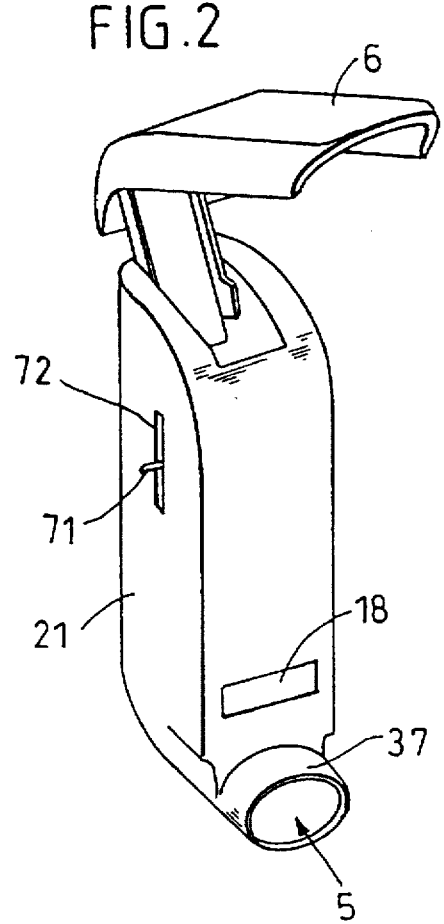
FIG. 2 is a perspective view of the device of FIG. 1, in its open position.

In the embodiment shown in the drawings, the device of the invention comprises a housing 21 provided with a cover 6, as can be seen in FIGS. 1 and 2. The housing 21 includes an endpiece 37 constituting a nose piece or a mouth piece, which defines an inhale duct 5. The housing 21 also includes a screen 18 suitable for displaying various messages to a patient using the appliance. The cover 6 is rotatably mounted on the housing 21 so as to be movable between a closed position (FIG. 1) in which it covers the endpiece 37, and an open position (FIG. 2) in which it reveals the endpiece 37.

Figure 8:
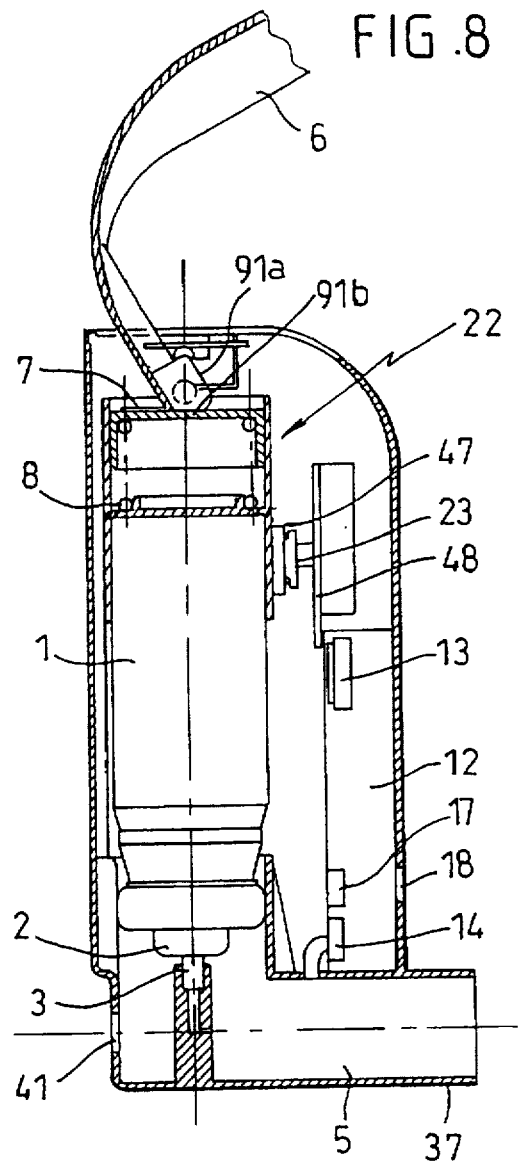
FIG. 8 is a view similar to FIG. 7, but after inhaling.

The device of FIGS. 1 and 2 is visible in greater detail in FIG. 4. In the example shown, the device includes an aerosol spray comprising a tank 1 that contains an active substance (a medicine) mixed with a liquefied propellant gas, a metering or "dosing" valve 2 crimped on the tank 1, and a hollow actuator rod 3 that is provided with an outlet end 4. In the particular example shown, the metering valve 2 is of the type that is suitable for operating in the upside-down position, however the metering valve 2 could equally well be of the type that operates in the rightway-up position, or it could be replaced by a pump or by some other dispenser means. The actuator rod 3 is movable between a rest position as shown in FIG. 4, and an actuated position as shown in FIG. 8 in which the actuator rod 3 is pressed into the metering valve 2. When the actuator rod 3 is displaced from its rest position to its actuated position, a metered quantity (or "dose") of active substance is issued via the outlet end 4 of the actuator rod. In conventional manner, the actuator rod 3 is returned resiliently towards its rest position by an internal return spring (not shown).

As can be seen in FIGS. 4 and 4a, the outlet end 4 of the actuator rod 3 is engaged in a blind bore 39 of a peg 38 disposed in the inhale duct 5. The blind bore 39 opens out into the inhale duct 5 via a lateral orifice 40 of small section pointing towards the endpiece 37.

The inhale duct also includes an air inlet orifice 41 that enables a flow of air to be established when a patient sucks into the inhale duct 5 via the endpiece 3.

In the example shown, the tank 1, the metering valve 2, and the actuator rod 3 are circularly symmetrical about an axis 25. The tank 1 has an end wall 1a having a cylinder 22 engaged thereover. The cylinder 22 has a cylindrical side wall 22a and an end wall 22b that covers the end wall 1a of the tank 1. Running from the end wall 22b of the cylinder 22, a cylindrical side wall 24 for guidance purposes that is circularly symmetrical about the axis 25 extends a certain distance away from the tank 1. A piston 7 is mounted to be axially slidable in the guide wall 24, and a compression spring 8 is disposed between the end wall 22b and the piston 7. The piston 7 preferably slides without sealing inside the guiding side wall 24 so as to prevent axial displacements of the piston 7 establishing pressure increases or decreases in the air in the gap between the piston 7 and the end wall 22b of the cylinder 22.

The cylinder 22 is adapted to slide in the housing parallel to the axis 25. It is guided in its sliding movement by three guide ribs, only two of which are shown, i.e. 73, 74, of the housing 21, which ribs extend parallel to the axis 25 (see FIG. 5). In addition, the side wall 22a and the cylinder 22 also includes two axial ribs (not shown) which cooperate with one of the three ribs to fix the position of the cylinder 22 with respect to rotation about the axis 25.

Figure 3:
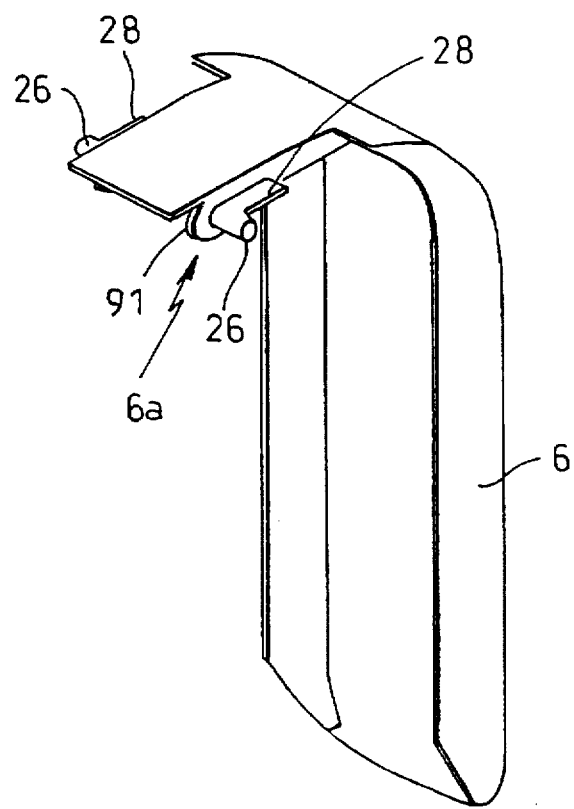
FIG. 3 is a perspective view of the cover of the FIG. 1 device.

As shown in FIG. 3, the cover 6 is rotatably mounted on the housing 21 by means of two pivots 26. In addition, in the vicinity of the pivots 26, the cover 6 has two projecting plates 28 that extend outwards, and that are disposed horizontally when the cover is in the closed position shown in FIG. 4. In addition, the cover 6 includes, in the vicinity of each pivot 26, a bearing surface 91 that is in contact with the piston 7. As explained below, the projecting plate 28 co-operates with the bearing surface 91 to form a lever 6a enabling the compression spring 8 to be compressed.

As can be seen in FIGS. 5 and 6, the housing 21 includes two lateral guide paths 28 parallel to the axis 25, each receiving one of the pivots 26 of the cover 6. Each guide path 28 is formed in a portion of extra thickness 42 of the wall of the housing 21 and it extends between two axial ends 28a and 28b. In addition, for reasons that are explained in detail below, a disassembly channel 43 is also formed in the excess thickness 42, perpendicularly to the axis 25, and the disassembly channel 43 opens out into the guide path 28 at an intermediate position between its two axial ends 28a and 28b. Furthermore, the disassembly channel 43 communicates with an outlet well 44 extending parallel to the axis 25 and opening out in a top portion of the housing 21.

Furthermore, the housing 21 includes a plate 29 above each of the guide paths 28, which plate 29 projects inwards and is disposed perpendicularly to the axis 25. When the cover 6 is tilted from its closed position to its open position, the projecting plates 28 of the cover press beneath the projecting plates 29 of the housing so as to displace the pivots 26 downwards along their guide paths 28. During this movement, the bearing surfaces 91 of the cover 6 move the piston 7 downwards, thereby compressing the spring 8.

Figure 7:
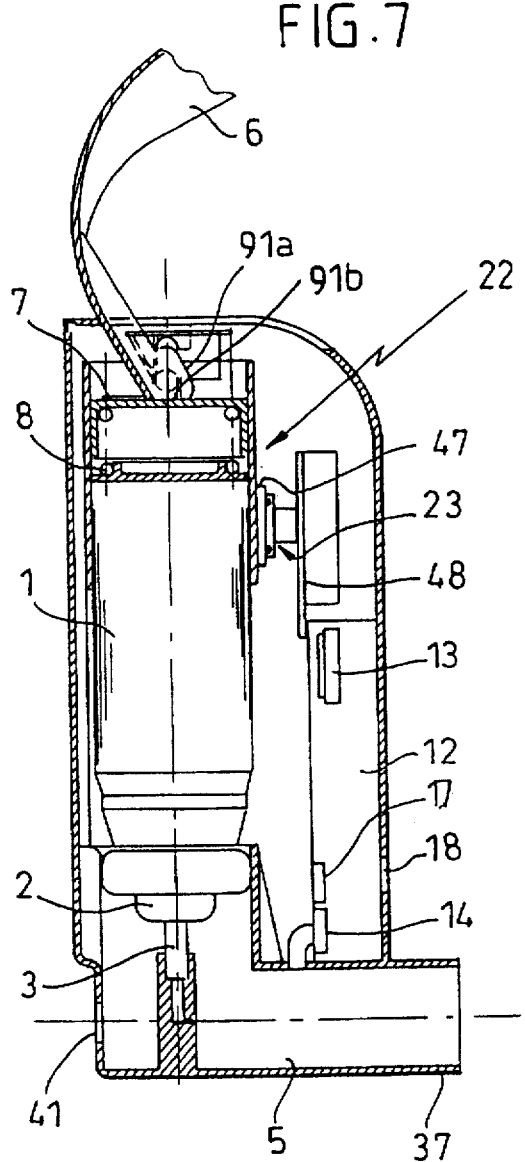
FIG. 7 is a section view similar to FIG. 4, but in the open position, prior to inhaling.

Advantageously, each thrust surface 91 of the cover 6 includes two flats 91a and 91b which bear against the piston 7 respectively when the cover 6 is in its closed position and when it is in its open position. When the spring 8 is compressed, as shown in FIG. 7, it urges the cylinder 22 and the tank 1 downwards, and it therefore urges the actuator rod 3 towards its actuated position. Nevertheless, the side wall 22b of the cylinder 22 includes an abutment member 47 which co-operates with a locking mechanism 23 so as to hold the cylinder 22 and the tank 1 in place so long as no suction has been detected in the inhale duct 15. The locking mechanism 23 is fixed on a plate 48 (e.g. a metal plate), and the plate is fixed inside the housing 21 by any known means, e.g. by screwing, by snap-fastening, etc. . . . .

Figure 11:
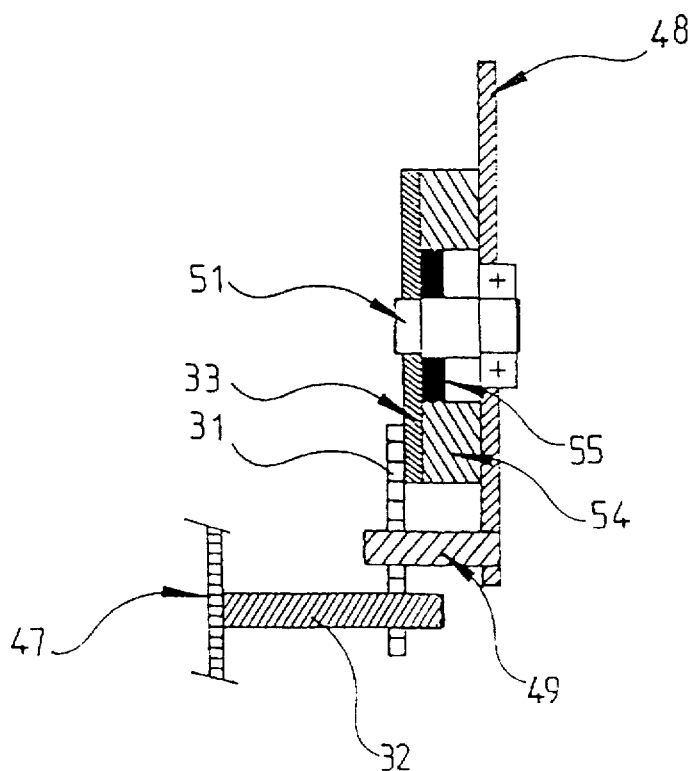
FIG. 11 is a cross-section view through the locking mechanism of the invention.
Figure 12:
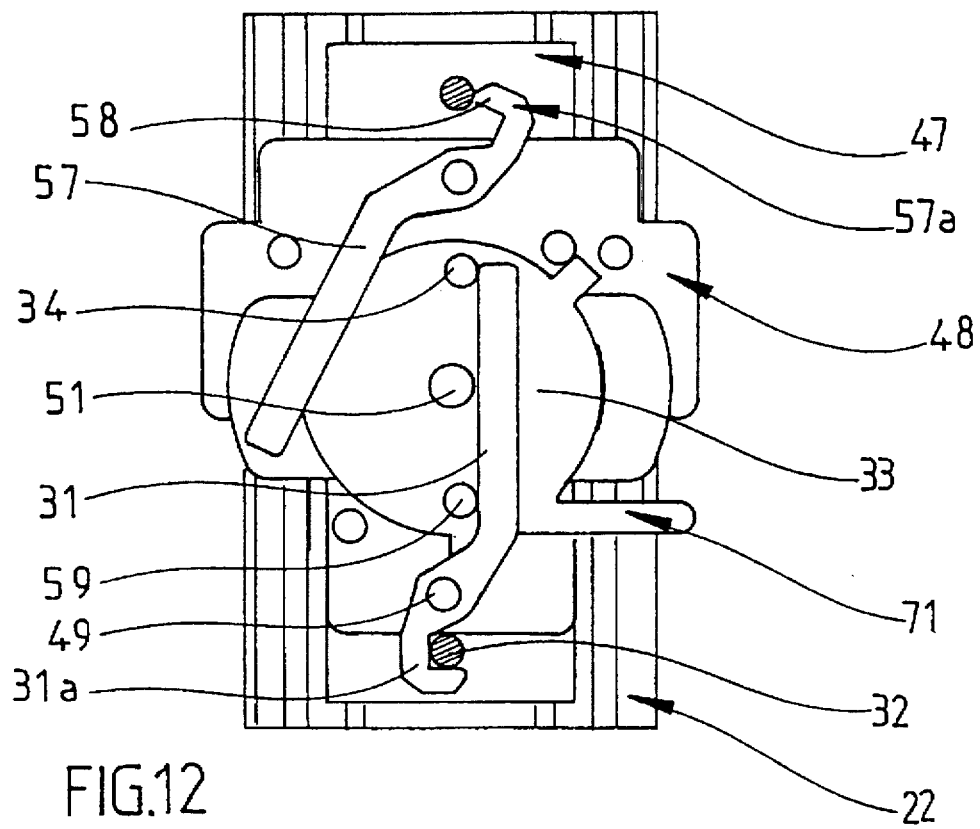
FIG. 12 is a plan view of the locking mechanism of another embodiment of the invention.
Figure 13:
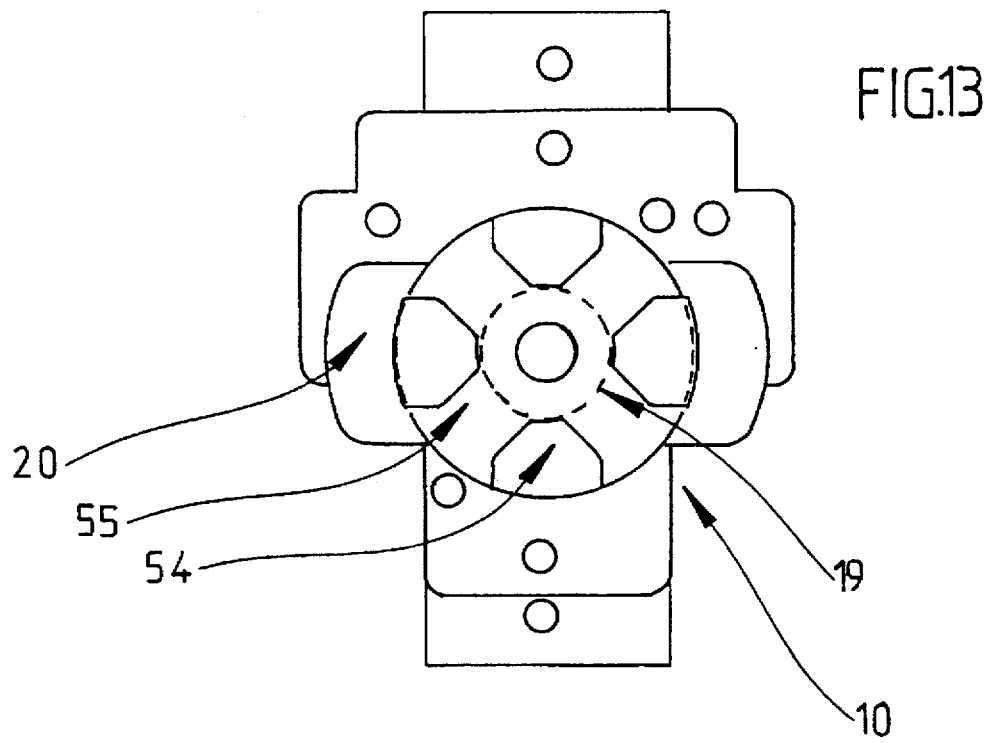
FIG. 13 is a view of the electromagnetic device of the locking mechanism of FIG. 12.

The locking mechanism is shown in greater detail in FIGS. 11, 12, and 13. It includes at least one latch member, advantageously a latching hook 31 that is mounted to rotate about an axis 49 secured to the plate 48. The latching hook includes a head 31a adapted to engage on a pin 32 of the abutment member 47 so as to lock the cylinder 22. The latching hook is thus movable between a latching position in which the head 31a is engaged on the pin 32, and a released position in which the head 31a no longer interferes with the abutment member 47, thereby releasing the cylinder 22.

The latching hook 31 is mounted to rotate about an axis 49 secured to the plate 48. There is also an axis 51 secured to said plate 48 and it has an armature 33 rotatably mounted thereon. On one surface, the armature includes a first stud 34 constituting a projection against which there bears that end of the latching hook 31 which is opposite from the head of the hook 31a. The other surface of the armature 33 faces an electromagnet 10. Advantageously, the electromagnet 10 comprises a four-pole magnet 19 and a coil 20, said magnet 19 including a stator flat 54 and bearing plates 55 that determine the polarization of said magnet.

The latching mechanism preferably also includes means for preventing the cylinder 22 of the tank 1 returning to its initial position prior to dispensing substance, thereby serving, in particular, to prevent reuse of the device over a certain lapse of time. These means advantageously comprise a second latching hook 57 (visible in FIG. 12) that is substantially identical to the first latching hook 31 and that is disposed symmetrically thereto about the axis 51 supporting the armature 33. The second latching hook 57 is also rotatably mounted on an axis 52 secured to the plate 48. It co-operates, via its head 57a, with a second pin 58 that is secured to the abutment member 47, and it is urged towards its released position by a second stud 59 that is symmetrically disposed relative to the first stud 34 on the armature 33, thereby enabling the cylinder to return towards its rest position.

Advantageously, the armature 33 includes an arm 71 that is accessible from outside the housing 21 through a slot 72 so as to enable said armature to be actuated manually, thereby displacing the locking member 31 into its released position, independently of any suction in the inhale duct.

Figure 9:
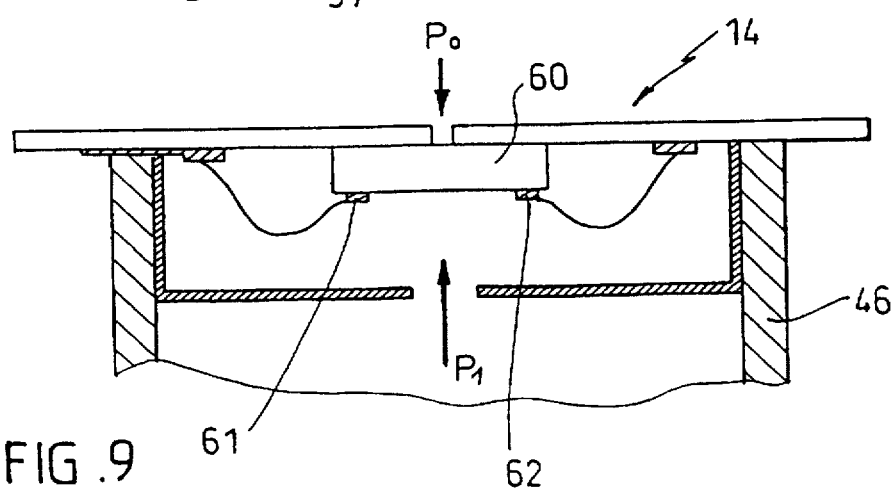
FIG. 9 is a diagrammatic section view showing the pressure sensor of the FIG. 1 device.

As shown diagrammatically in FIG. 4, the device of the invention also includes an electronic circuit 12 for controlling the coils 20 of the electromagnet 10, said electronic circuit 10 including one or more batteries or cells 13 for providing electricity, and being connected to a display screen 18 for controlling said display screen. In addition, the electronic circuit 12 includes a pressure sensor 14 suitable for metering the suction established in the inhale duct 5 by suction from a patient. In the example shown in FIG. 4, the inhale duct 5 includes an orifice 45 which is connected in sealed manner to the pressure sensor 14 via a flexible hose 46. As shown in FIG. 9, the pressure sensor may optionally include a silicon pellet 60 that is subjected on one face to atmospheric pressure and on its opposite face to the pressure that obtains inside the inhale duct. The silicon pellet 60 has a toggle point which is shifted by the difference between atmospheric pressure $P_0$ and the pressure $P_1$ that obtains inside the inhale duct, and that is subsequently brought back into balance. The silicon pellet 60 has two electrodes 61 and 62 connected to the electronic circuit 12 and providing said electronic circuit with a voltage signal representative of the suction that obtains within the inhale duct 5. A suitable pressure sensor for use in the above-specified situation is manufactured by the Swiss firm Keller Métrologie, and is sold under the reference OEM 0.2 bar. Similar pressure sensors can be obtained from the US firm NOVA (reference PH 0–15) or from the US firm ICS (model 30).

Figure 10:
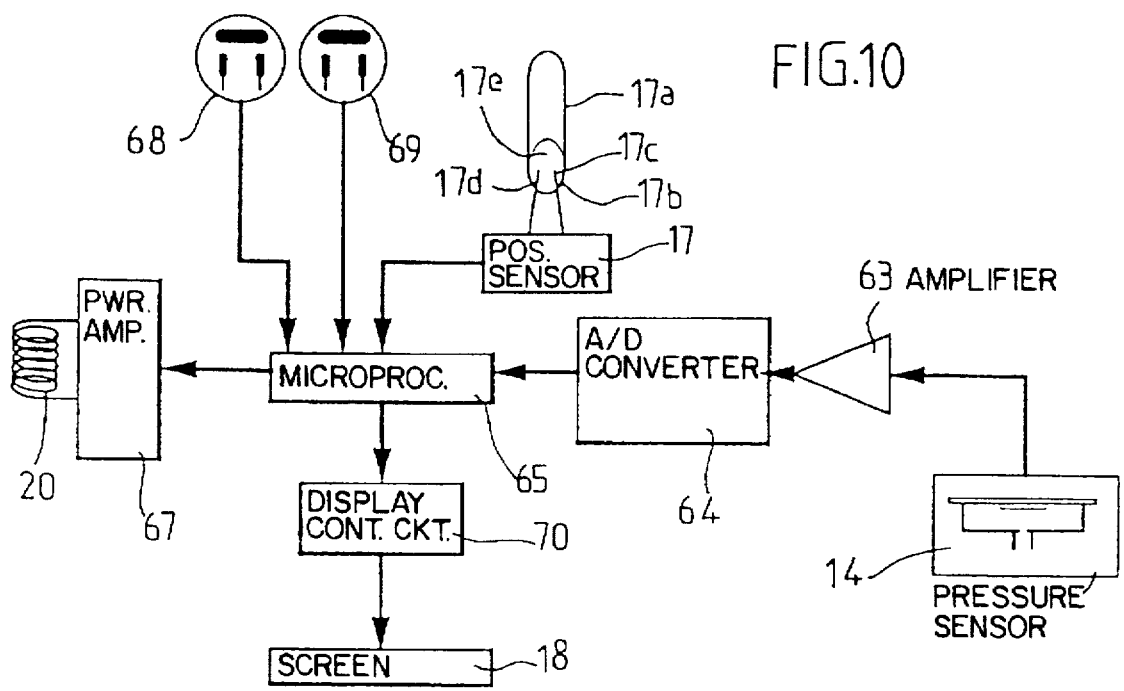
FIG. 10 is a block diagram of the electronic circuit of the device of FIG. 1.

As shown in FIG. 10, the electronic control circuit 12 includes a microprocessor 65 which is connected to the pressure sensor 14 via an amplifier 63 and an analog-to-digital converter 64. In addition, the microprocessor 65 is connected to a power amplifier 67 that controls the flow of current through the induction coils 20. The microprocessor is also advantageously connected to two contacts 68 and 69 respectively detecting full opening and full closing of the cover 6. The microprocessor 65 is also connected to a display control circuit 70 which is itself connected to the screen 18. Finally, the microprocessor 65 is connected to a position sensor 17 which may, for example, include a hollow glass column 17a in which a vacuum is established, and in which there flows a drop of mercury 17e. The column 17a has an end 17b which, when the appliance is in its proper position for use, constitutes a bottom end, and said bottom end 17b includes two contacts 17c and 17d which are wetted by the drop of mercury 17e when the appliance is in its proper position for use. One such position sensor is available from the US firm SAUNDERS under the reference 188 0001.

The device operates as follows. When the cover 6 is closed, as shown in FIGS. 1 and 4, the contact 69 informs the microprocessor 65 that the cover is closed, and the electronic circuit 12 is deactivated. When the patient opens the cover 6, as shown in FIG. 7, the spring 8 is compressed, as already explained above, so the cylinder 22 and the tank 1 are held in place against the force of the spring 8 by the latching hook 31, and the contact 68 informs the microprocessor 65 that the cover is open, thereby activating the electronic circuit 12 and switching on the display screen 18.

When the patient applies suction to the inhale duct 5, the pressure drop established in the inhale duct is detected by the pressure sensor 14 which sends a suction signal to the microprocessor 65 via the amplifier 63 and the analog-to-digital converter 64. In this example, the suction signal is an analog voltage signal whose value is proportional to the suction in the inhale duct 5. The microprocessor 65 thus receives the value of the suction in the inhale duct 5, and when said pressure reaches a predetermined value, the microprocessor causes the power amplifier 67 to send a pulse of current through the coils of the electromagnet. The current that passes through the induction coil 20 of the electromagnet is a DC current of polarity and magnitude suitable for overcoming or reducing the magnetic field created by the magnet core 19.

Because of this, the armature 33 in unstable equilibrium facing the four-pole magnet due to like poles being in opposition, is caused to rotate by a magnetic repulsion force towards its actuated position, with the stud 34 pushing the end of the latching hook 31 so that its head 31a no longer interferes with the pin 32 of the abutment member 47, such that the cylinder 22 is free to move downwards under drive from the compression spring 8, thereby entraining the tank 1. As a result, the actuator member 3 of the metering valve 2 moves from its rest position towards its actuated position, as shown in FIG. 8. A metered quantity of active substance (one "dose") is then sprayed into the inhale duct 5 via the metering valve 2, with said dose of active substance being inhaled by the patient.

In the event of an acute crisis, requiring several doses to be taken at intervals of time that are very close together, the patient may also actuate the device manually by tilting the forced actuator member 71 to bring said armature 33 into its actuated position, thereby causing spraying to take place into the inhale duct 5, as before.

When the user closes the cover 6, the spring 8 relaxes and the cylinder 22 is urged upwards together with the tank 1 under drive from the return spring (not shown) inside the metering valve 2, providing the electronic control circuit 12 has released the second latching hook 57. The actuator rod 3 thus returns to its rest position and the latching hook 31 returns to its latching position, with its head 31a being in engagement with the pin 32.

Advantageously, the microprocessor 65 of the electronic circuit 12 is programmed so as to avoid actuating the metering valve 2 in the event that the position sensor 17 fails to detect that the device is in its proper position. For example, the microprocessor 65 may trigger spraying only if the drop of mercury 17e is wetting both of the contacts 17d and 17c of the position sensor. This prevents a dose of propellant gas being sprayed into the inhale duct 5 without any active substance, or it prevents the metering valve 2 becoming unprimed. The use of a position sensor is not limited to a device having a metering valve that operates in the upsidedown position, as in the present case, but is equally applicable to devices having any preferred operating position.

In addition, it is necessary for the orientation of the device to be correct when the actuator rod passes from its actuated position to its rest position in order to avoid unpriming the valve. That is why, if the slope detector 17 detects wrong orientation at the moment when the cover is closed (when both contacts 68 and 69 are unactivated), after the device has been actuated, the screen 18 is used to display a message warning the patient that the next dose will be incomplete. The displayed message may also request the user to actuate the device manually once only by means of the lever 71 in order to reprime the metering valve. If the circuit 12 counts the doses it has issued, it is preferable to avoid counting such manual actuation as an issued dose.

Advantageously, the microprocessor 65 allows spraying to take place only if the device has been shaken within a predetermined length of time $T_2$ preceding inhalation by the patient. Advantageously, shaking of the device is detected by means of the position sensor 17, since shaking the device causes the drop 17e of mercury to move, thereby breaking and making electrical contact between the contacts 17c and 17d.

Advantageously, the microprocessor 65 is programmed to prevent the device being actuated until some predetermined length of time $T_1$ has elapsed since its most recent actuation, so as to avoid overdosing. The microprocessor 65 may optionally be programmed to count the number of doses it has issued, and to prevent the device being actuated if it has already issued some predetermined number $N_1$ of doses during a predetermined period $T_3$.

Advantageously, the microprocessor 65 stores in its memory the maximum number of doses of active substance contained in the tank 1, and the microprocessor 65 counts the number of doses issued by the device, with said microprocessor issuing a signal to the patient, e.g. a message that is displayed on the screen 18, when the number of doses issued has reached a predetermined threshold close to the maximum number of doses contained in the tank 1.

Advantageously, when the device is turned upsidedown so that the inhale duct 5 is above the tank 1, as detected by the position sensor 17, the microprocessor 65 is programmed to operate in calibration mode, in which case it does not actuate the device when the patient sucks in the inhale duct 5, but instead it determines the maximum suction $\Delta P_m$ that is established in the inhale duct during suction, after which the microprocessor 65 calculates and stores a trigger level of suction $\Delta P_0$ as a function of the maximum measured suction (e.g. a certain percentage of $\Delta P_m$), such that the device is subsequently actuated only if it is in the proper position for use and if the suction as measured in the inhale duct by the pressure sensor 14 is at least equal to said trigger level of suction $\Delta P_0$. Advantageously, under such circumstances, the microprocessor 65 is programmed to calculate the flow rate of air inhaled by the patient as a function of the suction measured in the inhale duct 5, and the microprocessor displays the inhaled air flow rate on the screen 18 so that the appliance also acts as a spirometer.

When the tank 1 is empty, it is possible to replace the tank 1 together with its metering valve 2 by means of a new tank 1. For this purpose, when the cover 6 is closed, as shown in FIG. 1, by pressing lightly on the top portion of the cover 6 while simultaneously urging said top portion 6b towards the endpiece 37, the pivots 26 of the cover 6 are caused to engage in the dismounting channels 43, thereby disengaging the pivots 26 via the outlet wells 44 (see FIG. 6). The cover 6 is thus separated from the housing 21 and the housing 21 has an opening 30 which is disengaged when the cover 6 is dismounted, the opening 30 being of sufficient size to give access to the inside of the housing 21 and to enable the cylinder 22, the tank 1, and the metering valve 2 to be removed, disengaging the actuator rod 3 from its bore 39. Advantageously, as shown in FIG. 4b, the free end of the guide wall 24 includes an inside lip 24a which holds the piston 7 in said guide wall 24 while the piston 7 is not in contact with the thrust surface 91 of the cover 6.

After removing the tank 1 and its metering valve 2, the cylinder 22 is disengaged and reengaged on the end of a new tank 1, and then the assembly is put back into place inside the housing, and the cover 6 is reinstalled on the housing 21.

FIGS. 14 and 15 show a variant of the device shown in the preceding figures, and it is not described in detail herein. In FIGS. 14 and 15, portions that are identical or similar to those of the device in the preceding figures are designated by the same references.

The device of FIGS. 14 and 15 differs from the device of the preceding figures in that the housing 21 includes an opening 83 in its bottom that is of sufficient size to allow the tank 1 together with its valve 2 to pass therethrough. The tank 1 and the valve 2 can slide freely along the axis 27 while the tank 1 is being removed, without interfering with the housing 21. The above-described peg 38 is secured to a disk 38a that is removably mounted in the opening 83. In the example shown, the disk 38a includes two studs 38c that project radially outwards and that can engage in two radially-inwardly open grooves 81 of the opening 83. Each of the grooves 81 also communicates with a downwardly-directed axial opening 80 in order to receive the studs 38c, which are subsequently engaged in the grooves 80 by rotation. The disk 38a may be rotated by means of a coin or of a screwdriver engaging in a slot 38b of the disk 38a. While the tank 1 is being extracted, the cylinder 22 is normally held in place by the locking mechanism, but it is also possible, optionally, to provide an abutment 82 that is secured to the housing 21 so as to prevent the cylinder 22 moving down together with the tank 1.

An advantage of the variant of FIGS. 14 and 15 is that it enables the peg 38 to be replaced each time the tank 1 is changed, thereby ensuring good hygiene for the appliance, and in particular good cleanliness for the lateral spray orifice 40.

In FIG. 14, the air inlet orifice has been omitted, air penetrating into the inhale duct 5 via the inside of the housing 21, passing around the valve 2 and the tank 1 which slides in non-sealed engagement in a guide well 84, thereby simplifying molding of the housing and avoiding the need to use an air filter.

In addition, the guide wall 24 of the FIG. 14 includes a vertical slot 24a in which there slides an appendix 7a of the piston 7, which appendix interferes with two switches 68 and 69 that constitute opening and closing contacts for the cover 6. This advantageous disposition may also be used with the embodiment shown in FIGS. 1 to 13.

Finally, the electronic circuit 12 of FIG. 14 includes a sensor 100 for detecting the presence of the tank 1 or of the metering valve 2. The sensor 100 may be an electrical contact or a field effect sensor (a proximity sensor). The sensor 100 can enable the dose counter to be reset to zero when the tank 1 and the metering valve 2 are replaced. The sensor 100 also enables the circuit 12 to count the number of tanks 1 that have already been used, so as to guarantee that the appliance is never used when purchased empty (i.e. without the tank 1 and its valve 2). The count of the number of tanks 1 that have already been used can also serve to prevent the appliance operating after some number of tanks 1 have been used. The sensor 100 may also prevent operation of the appliance if it does not detect the presence of the tank 1. The sensor 100 may be used in the embodiment of FIGS. 1 to 13.

What is claimed is:

1. A hand-held spray device actuated by inhaling, the device comprising:
    a housing;
    a tank of substance to be sprayed, said tank having an end wall with a cylinder engaged thereover;
    a dispenser device having an actuator member that is movable between a rest position and an actuated position, said dispenser device issuing a measured amount of said substance when the actuator member is displaced from its rest position to its actuated position, said actuator member being urged resiliently towards its rest position, the dispenser device also having an outlet for issuing said substance;
    an inhale duct through which a patient can suck in air, and which communicates with said outlet for said substance;
    actuator member urging means for urging said actuator member towards its actuated position;
    a locking mechanism fixed on a plate inside said housing, for holding said tank and said cylinder in place when no suction has been detected in said inhale duct, said locking mechanism including at least one latch member movable between a latching position in which said latch member locks said actuator member urging means, and a released position in which said latch member no longer locks said urging means; and
    unlocking means for displacing said latch member towards its released position while suction is being applied to said inhale duct;
    said unlocking means comprising:
        an electrical actuator for displacing said latch member;
        an electronic control circuit connected to said electrical actuator for the purpose of controlling it;
        a source of energy for powering said electronic control circuit; and
        a suction sensor for applying a suction signal to said electronic control circuit on detecting suction in the inhale duct, the electronic control circuit then causing the electrical actuator to displace the latch member into its released position;
    the device being characterized in that it further includes a position sensor for detecting any predetermined orientation of said device, in which said position sensor is connected to said electronic control circuit, and said electronic control circuit is adapted to trigger actuation of the device in said any predetermined orientation which is sensed by said position sensor.

2. A device according to claim 1, in which said suction sensor measures suction in said inhale duct relative to atmospheric pressure, and delivers a signal representative of the suction to the electronic control circuit.

3. A device according to claim 1, in which said position sensor includes means for detecting any predetermined orientation of the device and for causing said electronic control circuit to operate in a calibration mode, in which case the device is not actuated when the patient sucks from the inhale duct, but instead said electronic control circuit then determines the maximum amount of suction ($\Delta P_m$) set up in the inhale duct during suction, and it calculates and stores a trigger level of suction ($\Delta P_0$) as a function of said maximum suction ($\Delta P_m$), the device subsequently being actuated only when suction greater than or equal to said trigger level of suction ($\Delta P_0$) is detected in the inhale duct, and providing said electronic control circuit is not operating in its calibration mode.

4. A device according to claim 2, further including display means connected to the electronic control circuit to display a value for the air flow inhaled by the patient as a function of the suction measured in the inhale duct.

5. A device according to claim 1, including a shaking sensor for detecting shaking of said tank, in which said shaking sensor is connected to said electronic control circuit and said electronic control circuit is adapted to inhibit actuation of the device in the event of said tank not having been shaken during a second predetermined duration ($T_2$) preceding inhalation by the patient.

6. A device according to claim 1, in which the electronic control circuit is connected to warning means and said electronic control circuit is adapted to switch on the warning means to warn the patient that the device is not in any predetermined orientation for use, in the event that the position detector is not detecting the said any predetermined orientation.

7. A device according to claim 1, in which the substance to be sprayed is a liquid or a semi-liquid, the dispenser device is an aerosol valve or a pump, the electronic control circuit is connected to means for detecting displacement of the actuator member from its actuated position to its rest position, the electronic control circuit is connected to warning means, and said electronic control circuit is adapted to switch on the warning means, in the event that said displacement of the actuator member is detected while the device is not in its any predetermined orientation, to warn the patient that a next dose of said substance that the device dispenses will be incomplete.

8. A device according to claim 7, including means for actuating the valve or the pump manually, and in which said warning means tell the patient to actuate the valve or the pump manually for one occasion.

9. A device according to claim 7, including means for counting the number of doses of substance that are issued, and in which the issuing of said next dose is not counted.

10. A device according to claim 1, in which said position sensor includes a hollow column that extends vertically when the device is in its any predetermined orientation, said hollow column having a bottom end provided with two electrical contacts and said hollow column containing a drop of mercury which wets the two electrical contacts when the device is in its any predetermined orientation.

11. A device according to claim 10, in which said position sensor also serves as a shaking sensor, and said electronic control circuit is adapted to inhibit actuation of the device if said tank has not been shaken during a predetermined length of time ($T_2$) preceding inhalation by the patient.

12. A device according to claim 1, in which said electrical actuator includes an electromagnet, the latch member being in mechanical connection with an armature that is sensitive to magnetic fields, said armature being disposed facing said electromagnet, said electromagnet including a permanently magnetized core for maintaining said armature in a waiting position, said electromagnet further including a coil, and said electronic control circuit being adapted to power said coil with a current whose direction and magnitude are adapted to cause said armature to move into an actuated position, said armature thus driving the latch member from its latching position into its released position.

13. A device according to claim 12, in which the armature includes at least one stud co-operating with said latch member, said armature being mounted to rotate on a first axis and said latch member being mounted to rotate on a second axis, said first and second axes being secured to said plate, the stud driving the latch member in rotation from its latching position where it co-operates with a pin secured to the tank of substance to its released position.

14. A device according to claim 13, in which the electromagnet is a four-pole magnet and the armature is held in unstable equilibrium by opposing forces between identical poles while it is in its latching position, a signal from the electronic control circuit reducing an attraction force of the electromagnet in such a manner that the magnetic repulsion created by opposition between poles causes said armature to rotate towards its actuated position.

15. A device according to claim 12, in which a second latching member is provided that is rotatably mounted on a third axis secured to the plate, which member is substantially identical to the latch member and is disposed symmetrically relative to said latch member about a fourth axis supporting the armature, said second latch member cooperating with a second pin secured to the tank of substance and being driven into its released position by a second stud disposed symmetrically to the first stud on the armature, said second latch member preventing the dispenser device from returning to its rest position.

16. A device according to claim 12, in which the armature includes an arm extending outside the housing to enable said armature to be actuated manually, thereby enabling the latch member to be moved into its released position independently of any suction in the inhale duct.

17. A device according to claim 1, in which the dispenser device is secured to the tank of substance to be sprayed, the actuated position of the actuator member being such that said actuator member is moved towards said tank on passing from its rest position to its actuated position, the hand-held spray device including the housing secured to the inhale duct and to the actuator member, the handheld spray device further including a cover hinged on said housing and movable between a closed position in which it closes the inhale duct, and an open position in which it opens the inhale duct, the handheld spray device further including a compression spring adapted to urge the tank towards the actuator member to displace said actuator member into its actuated position, said compression spring having a first end which acts on the tank and a second end which acts on a thrust member, the cover including a lever-forming portion which bears against the thrust member when the cover is displaced into its open position, compressing the compression spring and said latch member locks the tank when it is in its latching position, the first end of the compression spring acts on an intermediate member fixed to said tank and said intermediate member includes a pin for receiving said latch member when it is in its latching position, said intermediate member then co-operating with the latch member to lock the tank.

18. A device according to claim 17, in which the actuator member is displaceable relative to the dispenser member parallel to an axis, the cover is mounted to rotate about two pivots, and the pivots are mounted in respective elongate guide paths parallel to the axis, the pivots thus being axially displaceable along their guide paths against the force of the compression spring, and the cover further including two lateral projections that are outwardly directed, and that co-operate with respective inwardly-directed projecting surfaces of the housing to constrain the pivots to move along their guide paths while compressing the compression spring when the cover passes from its closed position to its open position.

19. A device according to claim 18, in which the two guide paths include two axial ends and each has an opening disposed at the same level on both guide paths in a position that is intermediate between the two axial ends of each of the guide paths, to enable the pivots to escape from the guide paths when pressure is applied to the cover parallel to the axis, and simultaneously the cover is urged parallel to the axis towards said openings, the cover thus being removable from the housing, the housing including a loading opening of a size that enables the tank of substance together with its dispenser device to pass therethrough once the cover has been removed from the housing, the actuator member for the dispenser device being secured in removable manner to said housing, and the housing includes means for displacing the latch member into its released position independently of suction in the inhale duct.

20. A device according to claim 17, in which said lever-forming portion of the cover has a thrust surface in contact with the thrust member and said thrust surface includes two flats bearing against the thrust member respectively in the closed position and in the open position of the cover.

21. A device according to claim 17, in which the housing includes an opening of appropriate size to allow the tank together with its dispenser device to pass therethrough in order to be inserted into the housing or to be removed from the housing, and said housing further includes a support member which is secured to the actuator member and which is removably mounted in said opening.

22. A device according to claim 1, further including a sensor for detecting the presence of the tank and/or the dispenser device, said sensor being connected to the electronic control circuit to prevent operation of the device in the event of said tank being absent.

23. A device according to claim 1, further including a sensor for detecting the presence of the tank and/or of the dispenser device, said sensor being connected to the electronic control circuit, said electronic control circuit being adapted to count the number of tanks that have been installed in said device as a function of information from said sensor for detecting the presence thereof.

24. A device according to claim 23, in which said electronic control circuit is adapted to prevent the device being actuated if the number of tanks that have been installed in the device exceeds a predetermined number.

* * * * *